United States Patent [19]
Bianchi et al.

[11] Patent Number: 5,648,220
[45] Date of Patent: Jul. 15, 1997

[54] METHODS FOR LABELING INTRACYTOPLASMIC MOLECULES

[75] Inventors: Diana W. Bianchi, Brookline; Mary Ann DeMaria, Uxbridge, both of Mass.

[73] Assignee: New England Medical Center Hospitals, Inc., Boston, Mass.

[21] Appl. No.: 388,533

[22] Filed: Feb. 14, 1995

[51] Int. Cl.$^6$ .............................. C12N 5/00; G01N 33/53
[52] U.S. Cl. ...................... 435/7.1; 435/7.2; 435/7.25; 435/40.5; 435/962; 435/968; 436/8; 436/66; 436/174; 436/176; 436/548; 436/825
[58] Field of Search .......................... 435/7.1, 7.2, 7.25, 435/40.5, 40.51, 29, 968, 962; 436/8, 548, 66, 174, 176, 825

[56] References Cited

U.S. PATENT DOCUMENTS

| | | | |
|---|---|---|---|
| 4,910,131 | 3/1990 | Mellman et al. | 435/5 |
| 5,180,814 | 1/1993 | Hanna, Jr. et al. | 530/388.8 |
| 5,288,477 | 2/1994 | Bacus | 424/2 |
| 5,387,520 | 2/1995 | Lo Presti et al. | 435/240.2 |
| 5,411,861 | 5/1995 | Seed et al. | 435/6 |
| 5,422,277 | 6/1995 | Connelly et al. | 436/10 |

OTHER PUBLICATIONS

Berger et al., Simultaneous Detection of βGalactosidase Activity and Surface Antigen Expression in Viable Haematopoietic Cells, Cytometry 17:216–223, 1994.
Bianchi et al., Detection of fetal cells with 47, XY, + 21 karotype in maternal peripheral blood, Hum. Genet. 90:368–370, 1992.
Bianchi, Clinical Trials and Experience: Boston, Annals of the New York Academy of Sciences 731:92–102, 1994.
Bianchi et al., Erythroid-Specific Antibodies Enhance Detection of Fetal Nucleated Erythrocytes in Maternal Blood, Prenatal Diagnosis 13:293–300, 1993.
Bianchi et al., Isolation of fetal DNA from nucleated erythrocytes in maternal blood, Proc. Natl. Acad. Sci. USA 87:3279–3283, 1990.
Boyer et al., Fetal hemoglobin Restriction to a Few Erythocytes (F Cells) in Normal Human Adults, Science 188:361, 1975.
Brunch et al., Cellular Origins of the Fetal–Haemoglobin–Containing Cells of Normal Adults, The Lancet 1163–1165, 1979.
Clevenger et al., Quantitative Analysis of a Nuclear Antigen in Interphase and Mitotic Cells, Cytometry 8:280–286, 1987.
D'Alton et al., Current Problems in Obstetrics, Gynecology and Fertility XVII:41–80, 1994.
Geifman–Holtzman et al., Prenatal Genetic Diagnosis by Isolation and Analysis of fetal Cells Circulating in Maternal Blood, Seminars in Perinatology 18:366–375, 1994.
Jacobberger et al., Analysis of Intracellular Antigens by Flow Cytometry, Cytometry 7:356–364, 1986.
Kumar et al., Cell Separation: A Review, Pathology 16:53–62, 1984.

Papayannopoulou et al., Erythroid Progenitors Circulating in the Blood of Adult Individuals Produce Fetal Hemoglobin in Culture, Science 199:1349–1350, 1978.
Pembrey et al., Maternal Synthesis of Haemoglobin F in Pregnancy, The Lancet, Jun. 16, 1350–1354, 1973.
Parks et al., Flow Cytometry and Fluorescence–Activated Cell Sorting, Fundamental Immunology, Second Ed., Chapter 29, 781–802, 1989.
Pollice et al., Sequential Paraformaldehyde and Methanol Fixation for Simultaneous Flow Cytometric Analysis of DNA, Cell Surface Proteins, and Intracellular Proteins, Cytometry 13:432–444, 1992.
Popat et al., Pattern of Maternal F–Cell Production During Pregnancy, The Lancet, Aug. 30, 377–379, 1977.
Price et al., Prental diagnosis with fetal cells isolated from maternal blood by multiparameter flow cytometry, Am. J. Obstet. Gynecol. 165:1731–1737, 1991.
Schimenti et al., Fixation of Mammalian Cells for Flow Cytometric Evaluation of DNA Content Nuclear Immunofluorescence, Cytometry, 13:48–59, 1992.
Simpson et al., Isolating Fetal Cells From Maternal Blood – Advances in Prenatal Diagnosis Through Molecular Technology, JAMA 270:2357–2361, 1993.
Wachtel et al., Fetal cells in the maternal circulation: isolation by Multiparameter flow cytometry and confirmation by polymerase chain reaction, Human Reproduction 6:1466–1469, 1991.
Zheng et al., Prenatal diagnosis from maternal blood: simultaneous immunophenotyping and FISH of fetal nucleated erythrocytes isolated by negative magnetic cell sorting, J. Med. Genet. 30:1051–1056, 1993.
Schmid et al., "A Gentle Fixation and Permeabilization Method for Combined Cell Surface and Intracellular Staining with improved Precision in DNA Quantification,"Cytometry 12:279–285 (1981).
PCT/US96/01806 PCT search report mailed 11 Apr. 1996.
Y. Yheng et al., "Flow sorting of Fetal Erythroblasts using Intracytoplasmic Anti–Fetal Haemoglobin:Preliminary Observations on Maternal Samples," Prenatal Diagnosis 15:897–905 (1995).

(List continued on next page.)

Primary Examiner—Carol A. Spiegel
Attorney, Agent, or Firm—Fish & Richardson, P.C.

[57] ABSTRACT

The invention features a method of labeling a cell containing an intracytoplasmic target molecule involving (1) permeabilizing the plasma membrane of the cell so that (a) a reagent capable of detectably labeling the intracytoplasmic target molecule can traverse the plasma membrane into the cytoplasm of the cell; and (b) substantially all of the intracytoplasmic target molecule and the DNA of the cell remain in the cell; and (2) contacting the cell with the reagent to label the intracytoplasmic target molecule. The method may further involve detecting the label in the cell, and isolating the cell on the basis of detecting the label in the cell. The invention also includes cells permeabilized using the method of the invention.

9 Claims, No Drawings

OTHER PUBLICATIONS

S. Pipe et al., "Flow–Cytometric Detection of the RIX Subunit of Type I C–AMP–Dependent Protein Kinase in Human Cells," Cytometry 15:73–79 (1994).

Y. Ren et al., "Topology of Prostaglandin H Synthase–1 in the Endoplasmic Recticulum Membrane," Archives of Biochem. and Biophys. 323 (1):205–214 (1995).

A. Ruff–Roberts et al., "FISH on Flow–Sorted Cells," *Am. J. of Human Genetics*, 57(4):A287, No. 1671.

A Cazier et al, "Comparison of the Effects of a Preliminary Hepatic Washing and of Saponin on the Intracellular Penetration of Peroxidase–Labeled Anti–Rat Albumin Antibodies in Hepatocytes," Histochemistry 87:251–256 (1987).

K. Franek et al., "Reliable Method for the Simultaneous Detection of Cytoplasmic and Surface CD3E Expression in Murine Lymphoid Cells," Cytometry 17:224–236 (1994).

METHODS FOR LABELING INTRACYTOPLASMIC MOLECULES

BACKGROUND OF THE INVENTION

This invention relates to methods for labeling intracytoplasmic molecules.

Current methods for prenatal diagnosis at cellular and genetic levels involve invasive procedures such as amniocentesis and chorionic villus sampling (CVS). Because these methods involve small but significant chances of miscarriage, the current standard of care is to offer invasive prenatal diagnosis only to those women whose risk of a chromosomal or genetic abnormality is greater than or equal to the risk of a diagnostic procedure-related loss. Thus, prenatal diagnosis of chromosomal and genetic abnormalities is limited to a small portion of pregnant women. This is unfortunate, as the majority of abnormal newborns are born to women who were considered to have low risks (Geifman-Holtzman et al., *Seminars in Perinatology* 18(4):366–375, 1994; D'Alton et al., *Curr. Probl. Obstet. Gynecol. Fertil.* 17(2):44–78, 1994).

SUMMARY OF THE INVENTION

We have developed a method for permeabilizing the plasma membrane of a cell so that a molecule within the cell can be labeled. Detection of the labeled intracytoplasmic molecule in a biological sample can be used (1) to determine whether a cell containing the intracytoplasmic molecule is present in the sample, and (2) to facilitate isolation of a cell containing the intracytoplasmic target molecule from the sample for further analysis.

Accordingly, in one aspect, the invention features a method of labeling a cell containing an intracytoplasmic target molecule. In this method, the plasma membrane of the cell is permeabilized so that: (1) a reagent capable of detectably labeling the intracytoplasmic target molecule can traverse the plasma membrane into the cytoplasm of the cell, and (2) substantially all of the intracytoplasmic target molecule and the DNA of the cell remain in the cell. The cell is then contacted with the reagent to label the intracytoplasmic target molecule. By "substantially all of the intracytoplasmic target molecule and the DNA of the cell" is meant that preferably 50% or greater, more preferably 75% or greater, more preferably 85% or greater, more preferably 90% or greater, more preferably 95% or greater, and most preferably 99% or greater, of the intracytoplasmic target molecule and the DNA of the cell remain in the cell.

In one embodiment, the method further involves detecting the labeled intracytoplasmic molecule in the cell using standard methods, e.g., flow cytometry.

In another embodiment, the method further involves isolating the cell on the basis of detection of the labeled intracytoplasmic molecule in the cell. This can be achieved using standard methods in the art, e.g., fluorescence-activated cell sorting.

The cells labeled using the methods of the invention can be obtained from any biological sample (e.g., a blood sample (from e.g., a pregnant female) or a tissue homogenate), which can obtained from, e.g., any mammal including, but not limited to, humans, cows, horses, dogs, cats, sheep, goats, rabbits, rats, guinea pigs, hamsters, and mice.

Cells that can be labeled and, optionally, detected and/or isolated, using the methods of the invention include, but are not limited to, fetal nucleated erythrocytes (NRBC), fetal erythrocyte precursor cells, fetal hematopoietic stem cells, trophoblasts, fetal granulocytes, fetal leukocytes, tumor cells, cancer cells, and adult blood cells (e.g., leukocytes and red blood cells). However, any cell containing an intracellular target molecule that can be labeled may be isolated using the methods of the invention.

Reagents that can be used to label the intracytoplasmic molecules of the invention include, but are not limited to, antibodies, non-antibody proteins, and nucleic acids (such as DNA and/or RNA probes). The reagents either contain a label (e.g., a fluorescent molecule, such as fluorescein or rhodamine, a chemiluminescent tag, or biotin), or can be labeled by a secondary reagent (e.g., a secondary antibody) that contains a label.

The target molecules of the invention include any intracytoplasmic molecule (e.g., a protein or a nucleic acid) that is diagnostic for a target cell type. For example, a fetal cell-specific molecule, or a molecule present in both maternal and fetal cells, but characteristic of a fetal cell (e.g., fetal hemoglobin), can be used as a target molecule for detecting the presence of a fetal cell (e.g., a fetal nucleated erythrocyte (NRBC)) in a biological sample (e.g., a maternal blood sample). In addition, the intracytoplasmic target molecule can be hemoglobin or a hemoglobin variant. Hemoglobin variants that can be the target molecules of the invention include, but are not limited to, fetal hemoglobin, hemoglobin S, hemoglobin Lepore, hemoglobin H, and hemoglobin M (see, e.g., Rubenstein et al., (eds.) *Scientific American Medicine*, Scientific American, Inc. (New York, 1978), and references therein). Preferred target molecules of the invention are fetal hemoglobin and γ-globin. Other molecules that can be used as intracytoplasmic target molecules in the invention include cancer cell-specific molecules, or molecules that are present in both cancer cells and normal cells, but characteristic of cancer cells (e.g., terminal deoxynucleotidyl transferase (TDT) and the c-erbB2 protein). In addition, intracellular molecules that are diagnostic of infection by, e.g., bacteria or viruses (e.g., cytomegalovirus (CMV) pp65), may also be used as target molecules in the invention.

In a preferred embodiment, the plasma membrane of the cell is permeabilized by (1) incubating the cell at 25° C. to 40° C., preferably at 36° C. to 38° C., and most preferably at 37° C.; in about 2% to 8% by weight/volume, or preferably 4% by weight/volume, of paraformaldehyde; for 10 minutes to 4 hours, or preferably for 30 minutes to one hour. The cell is then permeabilized using standard methods by incubation in a solution containing alcohol. For example, the cell can be incubated at 1° C. to 8° C. (e.g., 4° C.) in methanol:acetone at a ratio of 0.1:1 to 1:0.1 volume/volume (e.g., 1:1), or in 20% to 90% by volume/volume methanol (e.g., 70%), for at least 15 minutes (e.g., for 1 to 2 hours).

In another aspect, the invention features a cell that contains an intracytoplasmic target molecule and is permeabilized so that: (1) a reagent capable of detectably labeling the intracytoplasmic target molecule can traverse the plasma membrane into the cytoplasm of the cell, and (2) substantially all of the intracytoplasmic target molecule and the DNA of the cell remain in the cell. The cell may be, e.g., a fetal cell, such as a fetal nucleated erythrocyte, a fetal erythrocyte precursor, or a fetal hematopoietic stem cell. Other examples of cells included in the invention, intracytoplasmic target molecules within these cells, and reagents and labels used to label the intracytoplasmic target molecules within the cells, are listed above.

The methods of the invention allow single-cell genetic and chromosomal analysis which can be used for, e.g., prenatal diagnosis. Prenatal diagnosis carried out using the methods of the invention allows screening for chromosomal and genetic abnormalities without incurring the risks, costs, and relative discomfort of invasive procedures, such as amniocentesis and CVS. Thus, the methods of the invention allow prenatal diagnosis of chromosomal and genetic abnormalities to be offered to all pregnant women, rather than being limited to high risk pregnancies. This is particularly important considering that pregnant women who are characterized as being at low risk, and thus are not routinely evaluated for these abnormalities, give birth to the majority of abnormal newborns. For example, 80% of infants having Downs Syndrome are born to women who are under the age of 35, and thus are not routinely tested for this abnormality.

Other features and advantages of the invention will be apparent from the following description of the preferred embodiments thereof, and from the claims.

DETAILED DESCRIPTION

The invention provides methods for detecting a rare cell (a target cell) in a biological sample based on labeling a target molecule within the cell. Once a cell is detected by these methods, it can be isolated using standard methods, and subject to further analysis.

A central feature of the invention is the method used to permeabilize the plasma membrane of the target cell so that the intracytoplasmic target molecule can be labeled. A cell treated by this method has two characteristics that are essential for the efficacy of the invention. First, the plasma membrane is sufficiently permeable so that a reagent capable of detectably labeling the target molecule is able to traverse the plasma membrane into the cytoplasm. Second, the plasma membrane is sufficiently intact so that substantially all of the intracytoplasmic target molecule and the DNA of the target cell remain in the cell.

The permeabilization method is carried out briefly as follows. A cell preparation containing (or suspected of containing) a target cell is incubated in about 2% to 8% by weight/volume (preferably 4% by weight/volume) paraformaldehyde for around 10 minutes to 4 hours (preferably for 30 minutes to 1 hour) at about 25° C.–40° C. (preferably at about 36° C. to 38° C., more preferably at 37° C.), and then is incubated permeabilized in a solution containing alcohol. For example, the cell may be permeabilized by incubation in methanol:acetone at a volume/volume ratio of 0.1:1 to 1:0.1 (e.g., 1:1), or in 20% to 90% volume/volume methanol (e.g., 70%), for around 1 to 24 hours at about 3° C. to 5° C. (preferably about 4° C.). The cells are then washed and contacted with a reagent (e.g., an antibody) that labels the intracellular target molecule. Detection of the label bound to the intracytoplasmic target molecule can then be used for detecting and/or isolating the target cell from the cell preparation.

Any intracytoplasmic molecule (e.g., a protein or a nucleic acid) that is diagnostic for a target cell type may be used as the intracytoplasmic target molecule in the methods of the invention. For example, a fetal cell-specific molecule, or a molecule present in both maternal and fetal cells, but characteristic of a fetal cell (e.g., fetal hemoglobin), can be used as a target molecule for detecting the presence of a fetal cell (e.g., a fetal nucleated erythrocyte (NRBC)) in a biological sample (e.g., a maternal blood sample). Detection of the labeled target molecule allows isolation of the fetal cell and subsequent genetic analysis of the cell, which can be used for prenatal diagnosis.

Other molecules that can be used as intracytoplasmic target molecules in the invention include cancer cell-specific molecules, or molecules that are present in both cancer cells and normal cells, but characteristic of cancer cells. Detection of these molecules in a biological sample (e.g., blood, lymph, or a cell suspension derived from a tissue sample) can be used to diagnose cancer or to monitor the progress of anti-cancer treatment. For example, terminal deoxynucleotidyl transferase (TDT) can be used as a target molecule for diagnosis of acute myeloid leukemia, while the c-erbB2 protein can be used as a target molecule for diagnosis of breast cancer.

Infectious diseases caused by, e.g., bacteria or viruses may also be diagnosed and/or monitored using the method of the invention. For example, detection of cytomegalovirus (CMV) pp65 in white blood cells can be used to diagnose CMV infection. Other uses for the methods of the invention include identification of carriers of recessive genetic diseases characterized by abnormal intracytoplasmic molecules, and characterization of tissues (e.g., bone marrow) being used for transplantation.

Reagents used to label the intracytoplasmic target molecules include, but are not limited to, antibodies, non-antibody proteins, and nucleic acids. The reagents can contain any of a number of labels that are known in the art including, but not limited to, fluorescent labels, such as fluorescein (e.g., fluorescein isothiocyanate (FITC)) or rhodamine, biotin, or magnetic particles. The reagent (e.g., a primary antibody) that binds to the intracytoplasmic molecule may not itself contain a detectable label, but may be detected by using a labeled secondary reagent (e.g., a secondary antibody) that binds to the primary reagent (see, e.g., Coligan et al. (eds.), *Current Protocols in Immunology*, John Wiley & Sons, Inc., 1994).

Detection of a labeled intracytoplasmic target molecule, and isolation of a cell containing it, can be carried out using standard methods in the art. For example, detection of the labeled cell can be carried out using flow cytometry methods (see e.g., Parks et al., Flow Cytometry and Fluorescence-Activated Cell Sorting, *In Fundamental Immunology*, second edition (W. E. Paul, Ed.) Raven Press, New York, 1989, 781–802; Coligan et al. (eds.), *Current Protocols in Immunology*, John Wiley & Sons, Inc., 1994). Isolation of cells containing the labeled intracytoplasmic molecules can be carried out using any of a number of standard methods in the art, including, but not limited to, fluorescence-activated cell sorting (FACS) and magnetic systems for isolating cells, e.g., magnetic-activated cell sorting (MACS). In addition, immunomagnetic beads and antibody-conjugated columns can be used (see, e.g., Parks et al., supra; Zheng et al., *J. Med. Genet.* 30:1051–1056, 1993).

In the case of, e.g., a cancer-specific intracytoplasmic target molecule, detection of a cell containing the target molecule in a biological sample may be by itself diagnostic. In the case of, e.g., detecting a fetal cell in a maternal blood sample, further analysis (e.g., genetic, chromosomal, or morphologic analysis) of the isolated cell may be required in order to reach a diagnosis.

Genetic analysis of isolated cells can be carried out using standard methods in the art, including, but not limited to, the polymerase chain reaction (PCR) (see, e.g., Geifman-Holtzman et al., supra). This method can be used to detect any type of genetic or chromosomal change that results in a disease, e.g., Cystic Fibrosis, Tay-Sachs disease, Gaucher disease, hemoglobinopathies, Duchenne muscular dystrophy, Lesch-Nyhan syndrome, and Sickle cell anemia. This method can also be used for determining the sex or rhesus factor status of a fetus (Geifman-Holtzman et al., supra).

Chromosomal abnormalities (e.g., aneuploidy, chromosomal rearrangements, and chromosomal deletions) in an isolated cell, e.g., a fetal NRBC, can be detected using fluorescence in situ hybridization (FISH; Geifman-Holtzman et al., supra). This technique relies on the hybridization of chromosome-specific nucleic acid probes to a particular chromosome of interest. For example, when used in conjunction with a fluorescent dye, chromosome-specific probes can be used to determine the numbers of copies of a given chromosome in an interphase nucleus. Each chromosome is detected as a colored dot, and the number of dots indicates the number of copies present of the specific chromosome. For example, a cell from an individual with trisomy 21 will show three dots after hybridization with a chromosome 21 probe set (Bianchi, Fetal Cells in Maternal Blood: Prospects for Noninvasive Prenatal Diagnosis, *In Annals of the New York Academy of Sciences* 731:92–102, 1994; Geifman-Holtzman et al., supra). Similarly, nucleic acid probes may be used in this method to detect chromosomal rearrangements or deletions. Thus, any condition characterized by aneuploidy (e.g., trisomy 21, trisomy 18, trisomy 13, and Kleinfelter syndrome), chromosomal rearrangement, or chromosomal deletion, may be diagnosed using this method.

The following example is meant to illustrate, but not to limit, the methods of the invention. Modifications of the conditions and parameters set forth below that are apparent to one skilled in the art are included in the invention.

EXAMPLE

Isolation of Fetal Nucleated Erythrocytes (NRBCs) for Prenatal Diagnosis

The method of the invention can be used to isolate a fetal NRBC from a maternal blood sample for genetic analysis. The maternal blood sample is obtained using standard methods in the art, preferably, in the range of 4 weeks to 20 weeks gestation.

Isolation and Preparation of Mononuclear Cells

1. Mononuclear cells can be isolated from maternal blood using, e.g., a Ficoll-Paque (Pharmacia, Piscataway, N.J.) density gradient, or similar standard methods (see, e.g., Coligan et al. (eds.), *Current Protocols in Immunology*, John Wiley & Sons, Inc., 1994; Kumar et al., *Pathology* 16:53–62, 1984).

2. The mononuclear cells are resuspended in 1 ml 2% fetal calf serum (FCS) in PBS, and counted with a Coulter Counter. If the cell count is between $10\times10^6$ and $20\times10^6$ cells/ml, the cells are ready intracellular staining (step 3, below). If the cell count is less than $10\times10^6$, the cells may be spun down and resuspended in a smaller volume in order to bring the concentration to the correct range. If the count is greater than $20\times10^6$ cells/ml, the cells may be diluted in order to bring the concentration to the correct range.

Intracellular Staining Protocol

3. Aliquots of $2\times10^6$ cells (about 100 µl each) are put into separate tubes (10 tubes, according to the above volumes and cell counts).

4. 0.5 mls of 4% by weight/volume paraformaldehyde (or 3.5% to 8% weight/volume) are added to each tube, and the tubes are then vortexed vigorously. After incubation for about 30 minutes to 1 hour at 37° C., the cells are washed.

5. 0.5 mls 1:1 by volume/volume methanol:acetone (or 70% methanol) are added to each tube while vortexing vigorously, and the tubes are then incubated for 1 hour to overnight at 4° C. The cells are then washed.

6. Approximately 1 µg/$2\times10^6$ cells of anti-gamma Hb FITC is added to each tube, which is then vortexed, and incubated for about 30 minutes at 4° C. The cells are then pelleted and washed.

7. The cells are then resuspended in 0.5 mls 2 µg/ml Hoechst 33342 in PBS, and stored at 4° C. until being sorted.

Other embodiments are within the following claims.

What is claimed is:

1. A method for isolating a fetal erythroid cell in suspension from a blood sample of a pregnant female, said fetal erythroid cell containing an intracytoplasmic target molecule, said method comprising the steps of:

(a) permeabilizing plasma membrane of said fetal erythroid cell such that (i) a directly or indirectly labeled reagent capable of specifically binding to said intracytoplasmic target molecule can traverse said plasma membrane into the cytoplasm of said fetal erythroid cell, and (ii) substantially all of said intracytoplasmic target molecule and DNA of said fetal erythroid cell remain in said fetal erythroid cell;

(b) contacting said permeabilized fetal erythroid cell with said directly or indirectly labeled reagent; and (c) isolating said fetal erythroid cell from said blood sample on the basis of detecting said label.

2. The method of claim 1, wherein said intracytoplasmic target molecule is fetal hemoglobin.

3. The method of claim 1, wherein said intracellular molecule is γ-globin.

4. The method of claim 1, wherein said label in said fetal erythroid cell is detected by flow cytometry.

5. The method of claim 1, wherein said fetal erythroid cell is isolated by fluorescence-activated cell sorting.

6. The method of claim 1, wherein said directly or indirectly labeled reagent comprises an antibody.

7. The method of claim 6, wherein said directly or indirectly labeled reagent comprises a fluorescent label or biotin.

8. The method of claim 1, wherein said permeabilizing step comprises:

a. incubating said fetal erythroid cell at 25° C. to 40° C. in 2–8% weight/volume paraformaldehyde for 10 minutes to 4 hours; and then b. incubating said fetal erythroid cell in a solution comprising alcohol 15 minutes to 3 hours.

9. The method of claim 8, wherein said incubating in step (a) is carried out at 37° C. in 4% weight/volume paraformaldehyde for 30 minutes to 1 hour.

* * * * *